United States Patent [19]

Marcus et al.

[11] Patent Number: 4,578,119
[45] Date of Patent: Mar. 25, 1986

[54] METHOD FOR CLEAN-UP OF BLOOD SPILLS

[76] Inventors: David L. Marcus, 317 E. 10th St., New York, N.Y. 10009; Peter F. Lordi, P.O. Box 902, Highland, N.Y. 12528

[21] Appl. No.: 549,498

[22] Filed: Nov. 7, 1983

Related U.S. Application Data

[62] Division of Ser. No. 413,061, Aug. 30, 1982.

[51] Int. Cl.⁴ .............................................. B08B 15/00
[52] U.S. Cl. ........................................... 134/4; 134/7; 252/194
[58] Field of Search ...................... 252/94, 95, 106, 88, 252/99, 155, 174.13, 174.25, 186.2, 186.35, 186.34, 187.26, 187.28, 187.34, 194; 424/149; 134/3, 7, 4

[56] References Cited

U.S. PATENT DOCUMENTS

| | | | |
|---|---|---|---|
| 1,613,448 | 1/1927 | Endres | 252/187.28 |
| 1,813,109 | 7/1931 | Banks | 424/149 |
| 2,020,228 | 11/1935 | Ashton | 134/7 |
| 3,250,720 | 5/1966 | Moore | 252/95 |
| 3,406,116 | 10/1968 | Vitale | 252/187.34 |
| 3,583,922 | 6/1971 | McClain | 252/95 |
| 3,702,826 | 11/1972 | Koceich et al. | 252/187.26 |
| 3,843,548 | 10/1974 | James | 252/187.26 |

OTHER PUBLICATIONS

"Functional Filters for Industrial Applications", Johns-Manville Filtration and Minerals Div., Denver, Colorado 80217, Jul. 1981.

"Celite Filter Aids for Maximum Clarity at Lowest Cost" Johns-Manville Filtration and Minerals Div., Denver, Colorado 80217, May 1981.

Bond, W. W., et al; "Viral Hepatitis B: Aspects of Environmental Control" Health and Human Services, vol. 14, No. 4, H.L.S. Oct., 1977, pp. 235-249, 252.

Primary Examiner—Richard V. Fisher
Assistant Examiner—W. Gary Jones
Attorney, Agent, or Firm—Sixbey, Friedman & Leedom

[57] ABSTRACT

A solid, pulverulent composition for destroying pathogen activity and absorbing liquid when placed in contact with blood spills consists essentially of a chlorine source capable of yielding hypochlorous acid in contact with water, such as calcium hypochlorite, and diatomaceous earth. The composition includes sufficient of the chlorine source to provide an available chlorine level in the composition of at least 5,000 ppm and, preferably, 5,000 to 65,000 ppm.

9 Claims, No Drawings

METHOD FOR CLEAN-UP OF BLOOD SPILLS

This application is a division of application Ser. No. 413,061 filed Aug. 30, 1982.

BACKGROUND OF THE INVENTION

1. Field of the Invention

The present invention relates to a composition and method for clean-up of blood spills and, more particularly, to the use of a solid, pulverulent composition for destroying pathogen activity and absorbing liquid in a blood spill.

2. Description of the Prior Art

In recent years it has become increasingly evident that direct or indirect exposure to contaminated blood is a major transmission mode for disease among patients and heath professionals. Although much has been written about the importance of asepsis in high disease risk environments, such as hospitals, most concern has been with control measures for bacterial and fungal contamination and considerably less attention has been given to control of viral infections. Yet, existing data indicates that viral infections, such as viral hepatitis type B, pose major disease problems and that many viruses, e.g., hepatitis B virus, are comparatively stable, particularly in blood plasma or serum, and are capable of withstanding exposure to wide ranges of temperature and humidity and a variety of chemical agents.

Inasmuch as the possibility of airborne transmission of viruses such as hepatitis is believed to be relaively small and since the consensus seems to be that exposure to contaminated blood is at least a major transmission mode for viral disease, an important companion to an active disease surveillance program is a vigorously enforced policy of immediate and thorough cleaning of all blood spills. To significantly reduce the risk of contamination, blood should never be allowed to remain on floors, walls, equipment, or other surfaces. In this connection, it has been found that hypochlorite solutions, among others, are effective virucidal agents for purposes of disinfection. The problem in their use has been devising a practical means for effectively applying the hypochlorite to the contaminated surface in a form which will optimize its disinfecting action. This problem is particularly acute in the case of blood spills on porous surfaces.

In the publication to W. W. Bond et al, *Viral Hepatitis B Aspects of Environmental Control,* 14 Health Laboratory Science 235 (October, 1977) it is taught that hypochlorite solutions having available chlorine concentrations in the range 500 to 5000 ppm are effective to destroy hepatitis B surface antigen reactivity and that the reactivity response of the antigen is at least indicative of the reactivity response of the hepatitis B virus. The antiseptic, germicidal and fungicidal properties of the hypochlorites have been well known for some time. Thus, in U.S. Pat. No. 1,813,109, Banks discloses a powdered antiseptic composition including a halogen generating substance combined with an absorbent medium, e.g., sodium hypochlorite and bentonite, particularly suitable for application to the human skin or mucous membrane surfaces. In U.S. Pat. No. 3,843,548, James discloses a paste or gel composition containing a source of hypochlorite ions, e.g., alkali metal hypochlorites, and a water absorptive clay comprising a synthetic magnesium silicate in which a proportion of the magnesium atoms are replaced by lithium atoms. The composition is said to have germicidal and fungicidal properties and to be useful for medical and veterinary purposes. U.S. Pat. No. 2,719,828 to MacMahon discloses a powdered composition containing calcium hypochlorite as a mustard gas decontaminating agent. Notwithstanding the varied disinfectant, germicidal and other uses for material such as the hypochlorites, no composition appears to be known from or suggested by the prior art which is effective, rapid and safe for inactivating pathogens in and faciliating clean-up of contaminated blood spills.

SUMMARY OF THE INVENTION

It is therefore an object of the present invention to provide a solid, pulverulent absorbent composition containing a source of available chlorine at a sufficient level to destroy the reactivity of viruses as well as to inactivate bacterial spores and a wide variety of other pathogens in blood spills.

It is another object of the present invention to provide an active chlorine containing solid, pulverulent composition which contains an absorbent substance effective for absorbing and facilitating the ready removal of blood spills by converting the spills to a substantially solid material.

It is still another object of the present invention to provide a solid pulverulent composition particularly effective in destroying pathogen activity in and absorbing blood spills, which composition provides a colorimetric indication that a pathogen inactivation reaction is occuring.

Other objects and advantages will become apparent from the following description and appended claims.

In accordance with the aforesaid objects the present invention provides a solid, pulverulent composition comprising a sufficient amount of a chlorine source capable of yielding hypochlorous acid in contact with water to provide an available chlorine level of at least 5000 ppm in the composition and a major proportion, by weight, of a water-absorptive diatomaceous earth. When brought into contact with a blood spill on a surface, the water in the blood spill reacts with the chlorine source to yield hypochlorous acid which destroys pathogenic activity and the highly absorbent diatomaceous earth converts the blood spill to a substantially solid material which can readily be removed from the surface and disposed of.

DESCRIPTION OF THE PREFERRED EMBODIMENTS

It has heretofore been the practice in the cleanup of blood spills first to physically remove the spill from the surface and then to destroy any remaining pathogen activity on the surface. Frequently this was done by absorbing the spill in paper towels until the surface was dry and then disinfecting or otherwise destroying pathogens on the dry surface. The wet, blood containing and pathogen contaminated towelling was carried away and disposed of by an unsuspecting health worker who, too frequently, suffered adverse consequences from exposure to the contaminating pathogen. It is the purpose of the unique composition and method of the present invention to avoid this unnecessary and undesirable exposure while at the same time performing the dual task of physically absorbing the blood spill from the surface to faciliate its removal and chemically destroying the pathogen activity. To accomplish these purposes the composition is desirably solid and pulverulent and contains a first component comprising a chlorine source capable of destroying pathogens in blood spills and a second component comprising an absorbent capable of converting a blood spill to a substantially solid and readily removable material. The absorbent, it will be appreciated, must be physically and chemically compatible with the chlorine source.

The chlorine source useful in the composition of the present invention is desirably in solid form, preferably pulverulent and capable of yielding hypochlorous acid in contact with ater. Inasmuch as blood is predominantly water, upon contacting a blood spill, the water reacts with the chlorine source to yield hypochlorous acid. The acid is a source of chlorine which, functioning as an oxidant, destroys the pathogen activity in the blood. During the oxidation reaction which inactivates the pathogen a color reaction takes place between the hypochlorous acid and the blood. The color of the blood changes from red to brown indicating that oxyhemoglobin (red) has been converted to methemoglobin (brown). At the same time the characteristic odor of released chlorine gas is detectable.

In order to effectively destroy substantially all pathogens in the blood, it is particularly desirable that the chlorine source provide an available chlorine level in the composition of at least 5,000 ppm, preferably in the range 5,000 to 65,000 ppm. One particularly important and useful source of chlorine are the strongly oxidative solid hypochlorites, such as calcium hypochlorite and lithium hypochlorite, particularly calcium hypochlorite which is readily available in solid form. A commercially available form of calcium hypochlorite found effective as a component of the present composition is available from the Olin Chemical Company. The liquid hypochlorites, such as sodium hypochlorite, are not desirable in the present invention since it is extremely difficult to convert these normally liquid compounds to solid form while retaining their ability to destroy pathogens. Another useful source of chlorine are the solid organic compounds which contain a thermodynamically stable nitrogen-chlorine bond, such as trichloroisocyanuric acid (1,3,5-trichloro-s-triazine-2,4,6-trione). Trichloroisocyanuric acid is commercially available from the Olin Chemical Company under the tradename Pace. Any of the chlorine sources suitable for use in the present composition may be used either alone, or in combination.

The absorbent component of the composition has been carefully selected to be totally compatible with the chlorine source while at the same time exhibiting superior absorbent characteristics. It is the function of this component to absorb the water in the blood spill, thereby rapidly converting the spill to a paste or putty, i.e., a substantially solid form, which can be readily confined in terms of the surface it contacts and contaminates and which is readily collectable and disposable. It has been found that a most effective absorbent for use in the composition of the present invention in diatomaceous earth. This material, in its commercially available forms, is capable of absorbing 60 to 100 times its own weight of water, relatively inexpensive, easy to work with, chemically passive to the chlorine source and generally harmless. Preferably, the diatomaceous earth is employed in a practical size which exhibits good flow properties, e.g., it is pourable, and is size compatible for ready and efficient mixing with the chlorine source. A diatomaceous earth particle for effective mixing, for example, with commercially available calcium hypochlorite has a size which is not too coarse yet not a fine powder, desirably about the particle size of ordinary table salt. One particularly useful diatomaceous earth product is available under the tradename Celite 560 from Johns-Manville Inc..

Celite 560 is a flux-calcined diatomite having a median particle size of 106 microns. One hundred percent (100%) by weight of the particles are finer than 250 microns but only 44 weight percent are finer than 90 microns, 30 weight percent are finer than 60 microns, 15 weight percent are finer than 40 microns and 7 weight percent are finer than 25 microns. Typically, Celite 560 has a composition of 89.6% $SiO_2$, 4.0% $Al_2O_3$, 1.3% $Fe_2O_3$, 3.3% $Na_2O$ and $K_2O$, 0.6% $MgO$, 0.5% $CaO$, 0.2% $TiO_2$ and 0.2% $P_2O_5$. It has a white color, a median pore size of about 22 microns, a dry density of about 19.5 lbs./ft$^3$ and a wet density of about 20 lbs./ft$^3$.

The composition of the present invention is readily formed by physically admixing the chlorine source and absorbent in relative proportions to yield a solid, pulverulent composition having an available chlorine level of at least 5,000 ppm and, preferably, 5,000 to 65,000 ppm. Inasmuch as studies have shown that 500–5,000 ppm available chlorine will destroy the reactivity of even the hepatitis antigen, it will be appreciated that, under all circumstances, the present composition provides sufficient pathogen destroying capability to deal with virtually any known pathogen in blood and, under most circumstances, the present composition provides a substantial excess of pathogen destroying capability. Although, subject to the foregoing limitation on minimum chlorine availability, there are no specific limitations on the relative proportions of each of the composition components, it should be appreciated that when brought into contact with a blood spill two competing processes occur with respect to the water content of the spill. On the one hand the water reacts with the chlorine source to yield hypochlorous acid. On the other hand the absorbent rapidly removes the water from the spill, making it unavailable to react with the chlorine source. Therefore, the proportions of components must be such that, taking into consideration the amount of water in the spill and notwithstanding absorption by the diatomaceous earth, there is sufficient of the chlorine source present to produce sufficient hypochlorous acid for pathogen destruction. It has been found that a particularly useful composition consists of about 10% by weight calcium hypochlorite, available from Olin Chemical Company, containing 65 to 68% active chlorine, and about 90% by weight Celite 560 diatomaceous earth, available from Johns-Manville, having an average particle size of 106 microns. The resulting composition provides about 65,000 ppm available chlorine for pathogen destruction and is a very effective, rapid absorbent.

The manner of use of the composition of the present invention to clean-up blood spills by absorbing the liquid and converting it to a readily collectable and disposable substantially solid form while, concurrently, destroying pathogen activity in the spill is quite simple. Generally, a supply of the composition will be maintained readily available in locations where blood spills are most likely to occur, e.g., blood or other laboratories, emergency rooms, operating rooms, and the like. Upon the occurence of a blood spill on a surface a sufficient amount of the powdered composition is poured onto the spill to absorb the liquid and convert the spill to a thick putty or paste, i.e., to a substantially solid material. At the same time, the water in the blood reacts with the chlorine source in the composition to yield hypochlorous acid which destroys pathogen activity in the spill. Thus, by simply pouring the composition onto the spill, the spill is physically contained and inhibited from spreading to contaminate a larger surface area, is converted to a substantially solid form and is inactivated insofar as pathogens in the spill are concerned. The inactivated, substantially solid material comprising the absorbed blood spill is readily removed from the surface using a small, disposable scoop. Both the inactivated, absorbed material and the scoop may be disposed of in conventional biohazard bags. When spills are dealt with in this manner, laboratory or other personnel never come into contact with either the contaminated blood spill, the inactivated, absorbed material or the equipment used during clean-up and disposal of the blood spill.

While the present invention has been described with reference to particular embodiments thereof, it will be understood that numerous modifications can be made by those skilled in the art without actually departing from the scope of the invention. Accordingly, all modifications and equivalents may be resorted to which fall within the scope of the invention as claimed.

We claim:

1. A method for absorbing liquid in and destroying the pathogen activity of pathogen contaminated blood spills from a surface without human exposure to the pathogens in the spill, comprising the steps of
   (a) contacting said blood spill with a solid, pulverulent composition for absorbing the liquid in the blood spill and physically containing the spill for inhibiting its spread on and further contamination of the surface, said solid pulverulent composition consisting essentially of a sufficient amount of a pourable particulate diatomaceous earth for absorbing the liquid in the blood spill and converting the spill to a substantially solid and readily removable form and a sufficient amount of a chlorine source which is physically and chemically compatible with said diatomaceous earth for providing an available chlorine level in said composition of at least 5,000 ppm;
   (b) forming hypochlorous acid by reaction of said chlorine source with water in said blood spill for destroying pathogen activity in said spill on contact therewith;
   (c) causing the blood in said spill to change color from red to brown for providing a color indication that pathogen destruction has occurred;
   (d) removing the resulting pathogenically inactivated, substantially solid material from the surface; and
   (e) disposing of said solid material.

2. A method, as claimed in claim 1, wherein said composition includes sufficient of said chlorine source to provide an available chlorine level in said composition of 5,000 to 65,000 ppm.

3. A method, as claimed in claim 2, wherein said diatomaceous earth median particle size is 106 microns.

4. A method, as claimed in claim 2, wherein said solid pulverulent composition consists of said particulate diatomaceous earth and said source of available chlorine.

5. A method, as claimed in claim 1, wherein said composition consists essentially of about 10% by weight chlorine source and about 90% by weight diatomaceous earth.

6. A method, as claimed in claim 1, wherein said diatomaceous earth median particle size is 106 microns.

7. A method, as claimed in claim 1, wherein said solid pulverulent composition consists of said particulate diatomaceous earth and said source of available chlorine.

8. A method, as claimed in claims 1, 2, 3, 4, 6 or 7, wherein said chlorine source is selected from the group consisting of lithium hypochlorite, calcium hypochlorite, solid organic compounds which contains a thermodynamically stable nitrogen-chlorine bond, and mixtures thereof.

9. A method, as claimed in claims 1, 2, 3, 4, 6 or 7, wherein said chlorine source is selected from the group consisting of calcium hypochlorite and trichloroisocyanuric acid.

* * * * *